US010245161B2

United States Patent
Bonin et al.

(10) Patent No.: US 10,245,161 B2
(45) Date of Patent: Apr. 2, 2019

(54) ASSEMBLY FOR IMPLANTING AN ACETABULAR CUP IN A COTYLOID CAVITY

(71) Applicants: DEDIENNE SANTE, Mauguio (FR); AXIOM, Lyons (FR)

(72) Inventors: Nicolas Bonin, Lyons (FR); Christian Manin, Decines (FR); Pierre-Yves Monfroy, Decines (FR); Jean-Michel Gaume, Mauguio (FR)

(73) Assignees: Dedienne Sante, Maugio (FR); AXIOM, Lyons (FR)

( * ) Notice: Subject to any disclaimer, the term of this patent is extended or adjusted under 35 U.S.C. 154(b) by 244 days.

(21) Appl. No.: 15/207,784

(22) Filed: Jul. 12, 2016

(65) Prior Publication Data

US 2018/0014948 A1 Jan. 18, 2018

(51) Int. Cl.
*A61F 2/46* (2006.01)
*A61F 2/30* (2006.01)

(52) U.S. Cl.
CPC .. *A61F 2/4609* (2013.01); *A61F 2002/30471* (2013.01); *A61F 2002/4624* (2013.01); *A61F 2002/4627* (2013.01); *A61F 2002/4628* (2013.01); *A61F 2002/4681* (2013.01)

(58) Field of Classification Search
CPC ............ A61F 2/4609; A61F 2002/4624; A61F 2002/4681
USPC ......................................... 606/91; 623/22.21
See application file for complete search history.

(56) References Cited

U.S. PATENT DOCUMENTS

| | | | |
|---|---|---|---|
| 6,468,281 B1 | 10/2002 | Badorf et al. | |
| 2007/0219562 A1 | 9/2007 | Slone et al. | |
| 2012/0053592 A1* | 3/2012 | Burgi | A61F 2/4609 606/91 |
| 2013/0079785 A1* | 3/2013 | Burgi | A61F 2/4609 606/91 |
| 2014/0228854 A1* | 8/2014 | Witt | A61B 17/1746 606/96 |
| 2015/0094729 A1* | 4/2015 | Schmit | A61F 2/4609 606/91 |
| 2015/0250615 A1* | 9/2015 | Biegun | A61F 2/4609 606/91 |
| 2016/0213492 A1* | 7/2016 | Castello | A61F 2/4609 |
| 2016/0331551 A1* | 11/2016 | Slade | A61F 2/4609 |

FOREIGN PATENT DOCUMENTS

WO WO8605384 9/1986
WO WO2004069107 8/2004

* cited by examiner

*Primary Examiner* — Matthew J Lawson
(74) *Attorney, Agent, or Firm* — Defillo & Associates, Inc.; Evelyn A. Defilo

(57) ABSTRACT

The present invention relates to an assembly having a acetabular cup has at least two snapping rims; the gripper is a subassembly separated from the handle, including a snapping teeth suitable for engaging with the snapping rims included by the acetabular cup. The gripper includes a movable pusher, capable, during its movement, of exerting thrust on the acetabular cup along the axis of revolution of said acetabular cup, so as to disengage the snapping rims comprised by the acetabular cup from their engagement with the snapping teeth included by the gripper; and the assembly includes an actuating device for actuating the movable pusher.

1 Claim, 5 Drawing Sheets

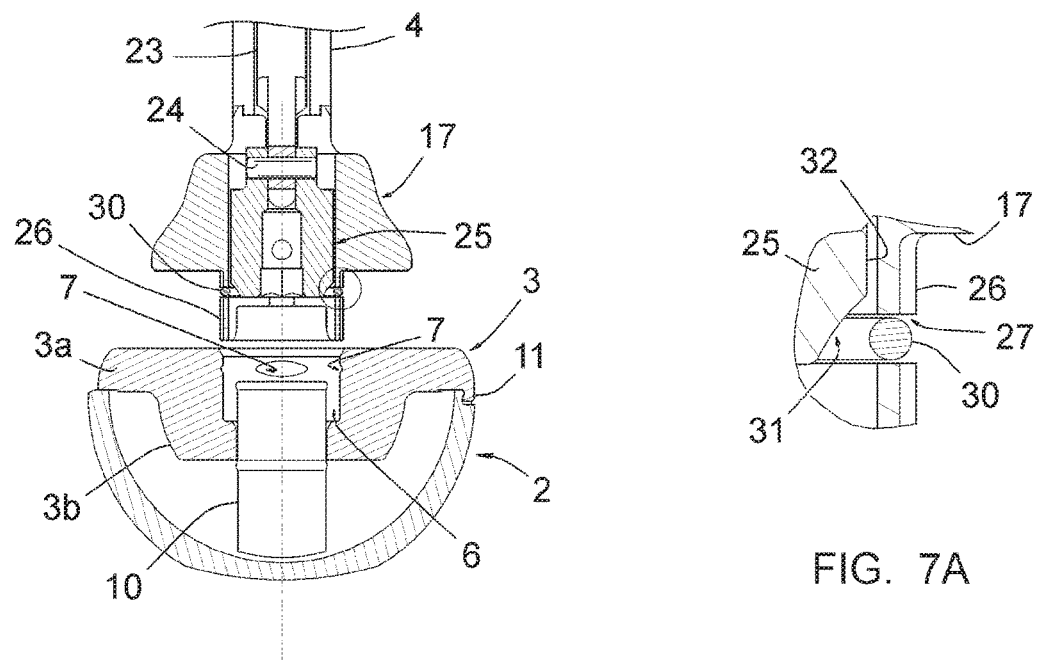
FIG. 7
FIG. 7A
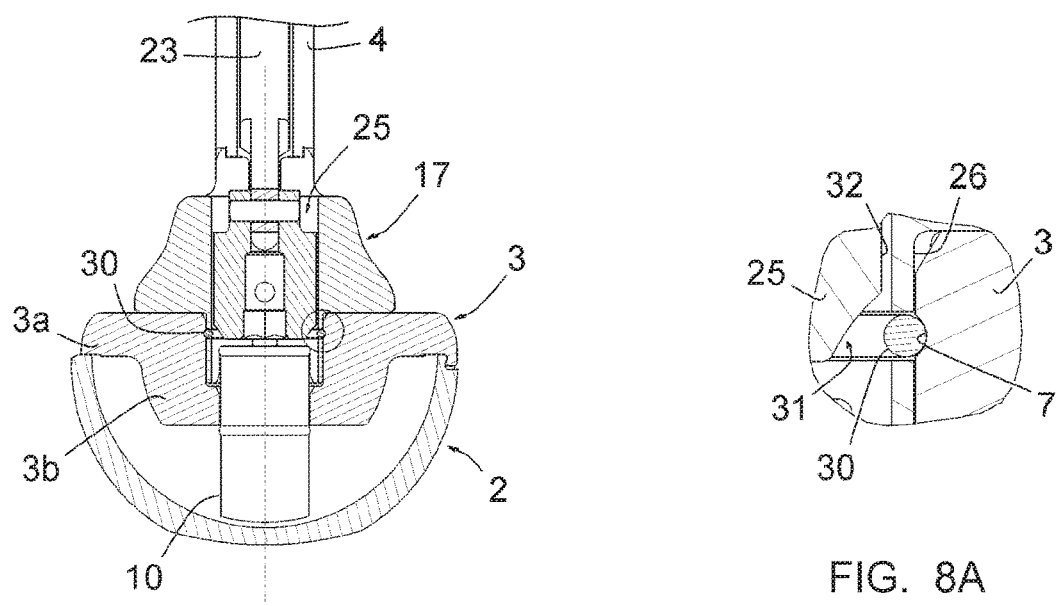
FIG. 8
FIG. 8A

ASSEMBLY FOR IMPLANTING AN ACETABULAR CUP IN A COTYLOID CAVITY

TECHNICAL FIELD

The present invention relates to an assembly for implanting an acetabular cup in a cotyloid cavity. The term "acetabular cup" used in the present description designates the outer part of a cotyloid implant, generally made from metal, intended to be impacted in said cotyloid cavity in a patient's pelvis. This cotyloid implant comprises, aside from this outer shell, and according to a well-known technique that does not need to be described, an inner sliding core, in particular made from high-density polyethylene, forming an articulation cavity for a femoral head supported by a femoral rod implanted in the femur.

BACKGROUND OF THE INVENTION

As one knows, a patient's pelvis bone may wear out over time at its parts defining the cotyloid cavity, thus requiring the placement of a cotyloid implant reforming the cotyloid cavity in order to receive the prosthetic femoral articulation head.

In order to be placed perfectly in the cotyloid cavity, the cotyloid implant must be impacted in a cavity, which is done using an instrument comprising a gripping head for the acetabular cup and a handling/impacting handle for that acetabular cup.

For example, patent application publication no. WO 2004/069107 describes an acetabular cup with a proximal inner groove and an instrument comprising a gripping head secured to a handle. The gripping head is equipped with radially movable locking tabs, which engage in the groove of the acetabular cup in order to assemble the acetabular cup thereon, and which are capable to be withdrawn using a handle, to release the acetabular cup.

Such an instrument has a complex structure, and is therefore expensive to manufacture. Furthermore, this instrument must be carefully sterilized between two surgical procedures, in particular at the many interstitial spaces comprised by the gripping head, which affects the usage cost of this instrument.

The present invention aims to resolve this drawback.

Patent application publications nos. US 2007/219562, WO 86/05384 and U.S. Pat. No. 6,468,281 describe similar instruments, with gripping heads secured to handles, these instruments further comprising distal bearing heads coming into contact with the bottom of the acetabular cups to distribute the impact force. The same comments as above can be made regarding the assemblies described by these documents.

OBJECT OF THE INVENTION

The present invention precisely aims to resolve the aforementioned drawbacks of the existing assemblies.

SUMMARY OF THE INVENTION

According to the invention, the assembly comprises:
an acetabular cup, intended to be implanted in a cotyloid cavity of a patient's pelvis, and
a gripping/impacting instrument for the acetabular cup, comprising:

a gripper, having an appropriate surface to come into contact with the acetabular cup, and equipped with reversible retaining members for reversibly retaining the acetabular cup, and
a gripping/impacting handle;
the acetabular cup has at least two snapping rims;
the gripper is a subassembly separated from the handle and capable to be assembled to said handle, comprising means for connecting to the handle;
the handle is a separate subassembly from the gripper and capable to be assembled to the gripper, comprising connecting means for connecting to the gripper, capable to cooperate with the connecting means comprised by the gripper to connect said handle to said gripper;
the reversible retaining members are in the form of snapping teeth suitable for engaging with the snapping rims comprised by the acetabular cup and releasing the acetabular cup following a thrust exerted on the acetabular cup substantially along the axis of revolution of that acetabular cup;
the gripper comprises a movable pusher, movable from a withdrawn position not hindering the assembly of the acetabular cup to the gripper, toward an extension position, this pusher exerting, during this movement, thrust on the acetabular cup substantially along the axis of revolution of said acetabular cup, so as to disengage the snapping rims comprised by the acetabular cup from their engagement with the snapping teeth comprised by the gripper; and
the assembly comprises means for actuating the movable pusher, making it possible to move that pusher from said withdrawn position to said extension position.

The gripper is thus formed by a subassembly separable from the handle, such that it is capable to be assembled to the acetabular cup by the manufacturer of the acetabular cup, then to be sterilized and packaged with that acetabular cup. During use, the practitioner opens this package and brings the respective connecting means of the handle and the gripper into a mutual assembly state, which allows him/her to form the gripping/impacting instrument for the acetabular cup; once the impacting is done, this practitioner acts on the actuating means of the pusher so as to move said pusher toward said extension position, and in so doing, to separate the acetabular cup from the gripper.

This instrument structure thus makes it possible to give the gripper a simplified structure, in particular making it possible for this gripper to be intended for a single use. As a result, the sterilization requirements for the instrument only relate to the handle, and are greatly reduced.

Furthermore, the assembly according to the invention allows the acetabular cup to be ejected from the gripper, therefore allowing a separation of the instrument and the acetabular cup that does not risk affecting the position of the acetabular cup in the equipped cavity.

The gripper may in particular be formed by a single part made by molding or machining a synthetic material, said snapping teeth being integral with the rest of the gripper.

This gripper is thus particularly inexpensive to produce.

It would be conceivable for said actuating means of the movable pusher to be of the piston or screwing/unscrewing type, for example acting through the handle, which would be tubular.

Furthermore, it would be conceivable for said connecting means connecting the handle to the gripper to be in the form of a screwed connection; for example, a tubular sleeve as cited above would be outwardly threaded and capable to be assembled to the gripper by screwing.

However, according to one preferred embodiment of the invention:

the connecting means for connecting the gripper to the handle comprise:

an assembly cavity arranged in the gripper and an assembly head secured to the handle, this assembly head forming an extension capable to be received in an adjusted manner in the assembly cavity;

first locking recesses arranged in the walls defining said assembly cavity and second locking recesses arranged in the side walls of said extension, the first and second recesses coming opposite one another in the assembly position of the gripper to the handle;

a movable locking/thrust part, capable to be moved in said extension, that forms third recesses capable to come opposite said second recesses, and that has flats situated near these third recesses, on the proximal side relative thereto;

an elastically deformable shank or other similar expansive element, engaged and retained in said first recesses or in said second recesses, this shank being deformable between a contracted state, in which it does not hinder the engagement and sliding of said extension in said assembly cavity, and a not deformed state, in which it extends both in said first recesses and in said second recesses, thus performing a reversible retention of said extension in said assembly cavity and therefore a reversible assembly of the gripper to the handle;

said locking/thrust part being movable between a position not locking the assembly of the gripper to the handle, in which said third recesses are opposite the shank and allow the deformation of said shank in said contracted state, therefore allowing said reversible assembly of the gripper to the handle, and a position locking the assembly of the gripper to the handle, in which said flats comprised by this locking/thrust part are opposite the shank and prohibit the deformation of said shank in said contracted state, therefore locking the assembly of the gripper to the handle;

said movable pusher is situated opposite said assembly cavity; and the actuating means of the pusher include said locking/thrust part, which is movable between said locking position and a bearing position in which it bears against the movable pusher so as to move said pusher toward said extension position.

Thus, the assembly of the handle to the gripper is done simply, by engaging said extension comprised by the assembly head in said assembly cavity, until the shank is engaged in said first and second recesses, by elastic return of said shank. The handle is then reversibly connected to the gripper, sufficiently to grasp the gripper-acetabular cup assembly and bring this assembly toward the cotyloid cavity to be equipped.

Once the impacting of the acetabular cup is done in the cotyloid cavity, the practitioner acts on the actuating means so as to move said locking/thrust part toward said locking position of the connection of the gripper to the handle, then toward said bearing position, so as to eject the acetabular cup. Consequently, the connection of the gripper to the handle is locked before the force necessary to eject the acetabular cup begins to be exerted on the connection of the acetabular cup to the gripper.

The invention thus provides connecting means that are easy to use, acting through simple inter-engagement, and the maintained engagement of which is provided automatically when the acetabular cup is ejected. There is therefore no risk of these connecting means releasing themselves rather than the snapping connection of the acetabular cup to the gripper being released.

It must be emphasized that for clarity of the present description, it has been stated that said assembly cavity is arranged on the gripper and said extension is arranged on the assembly head; it would in fact be conceivable for said cavity to be arranged in the assembly head and for the gripper to form said extension.

Preferably, said actuating means include, aside from said locking/thrust part, a lever mounted pivoting on the handle and a connecting rod connecting this lever to the locking/thrust part, said connecting rod performing, during the pivoting of the lever, the movement of said locking/thrust part between said non-locking and bearing positions.

According to one simple embodiment of the invention, the gripper comprises a bore in which the movable pusher is engaged and is capable to slide;

the movable pusher is formed by a cylindrical part having two circular ribs protruding from its wall, these ribs being situated at a distance from one another at least equal to the travel of the pusher between its aforementioned withdrawn and extended positions;

the gripper is made from a slightly elastically deformable material, such as a synthetic material, allowing the engagement of one of said circular ribs through said bore and the retention of the movable pusher on the gripper by elastic return of the material making up the gripper around the wall portion of the movable pusher situated between the two ribs.

The gripper and the movable pusher thus have simple structures, and the assembly of the movable pusher on the gripper is done simply.

Advantageously, the extension forms, at its end intended to be turned toward the movable pusher, a surrounding end-piece capable to engage on the movable pusher.

This engagement of the extension with the movable pusher ensures perfect guidance of this pusher when the locking/thrust part bears against this pusher during its movement.

The invention will be well understood, and other features and advantages thereof will appear, in reference to the appended diagrammatic drawing, described below; this drawing shows, as a non-limiting example, one preferred embodiment of the assembly in question.

BRIEF DESCRIPTION OF THE DRAWINGS

FIG. 7 is a sectional side view, passing through the axis of the acetabular cup, of an assembly head comprised by the handle, the gripper and the acetabular cup, in a non-assembly position of the head and the gripper, with a detail circled;

FIG. 7A is a view of the circled detail of FIG. 7;

FIGS. 8 and 8A are views similar to FIGS. 7 and 7A, respectively, in an unlocked assembly position of said assembly head to the gripper;

DESCRIPTION OF THE PREFERRED EMBODIMENTS

Figure 1:
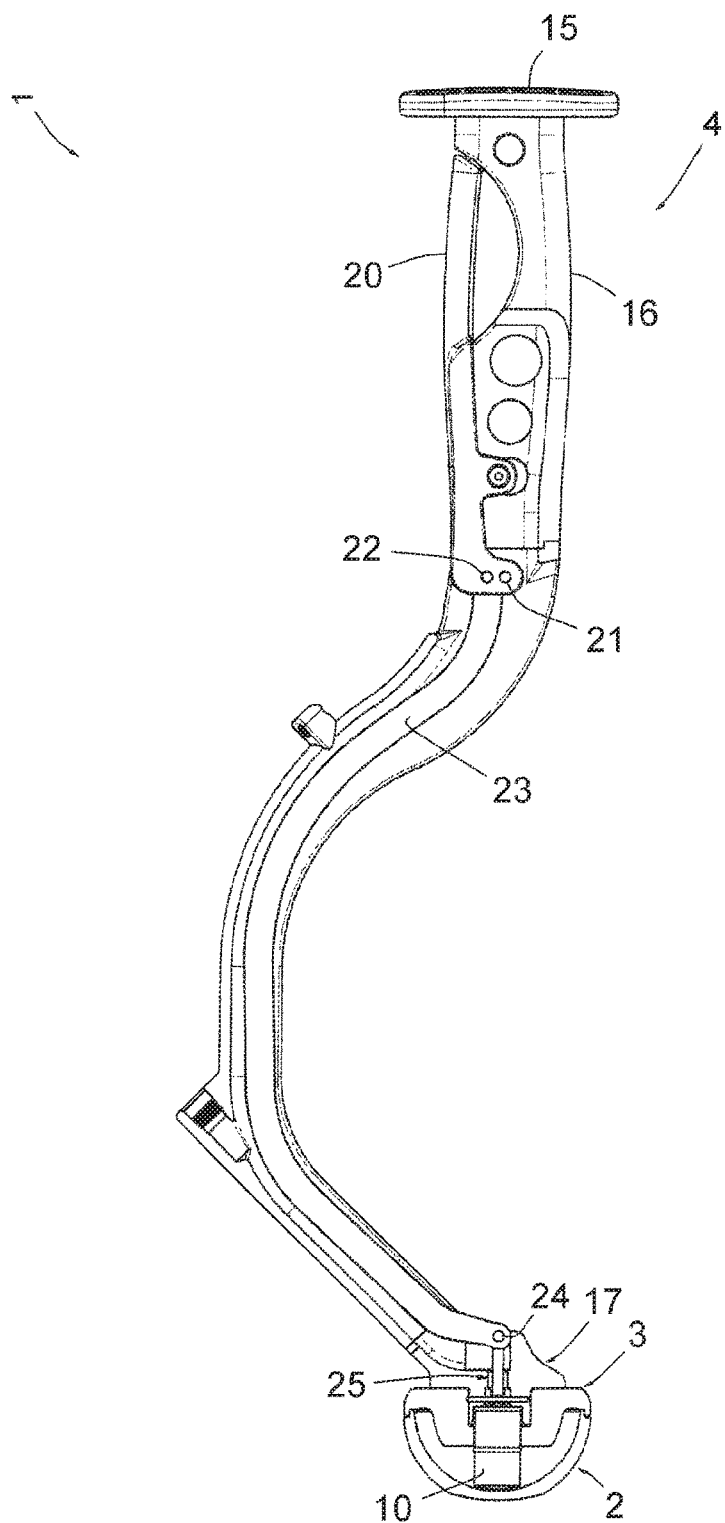
FIG. 1 is a side view of this assembly, in a first position of a lever that it comprises.
Figure 2:
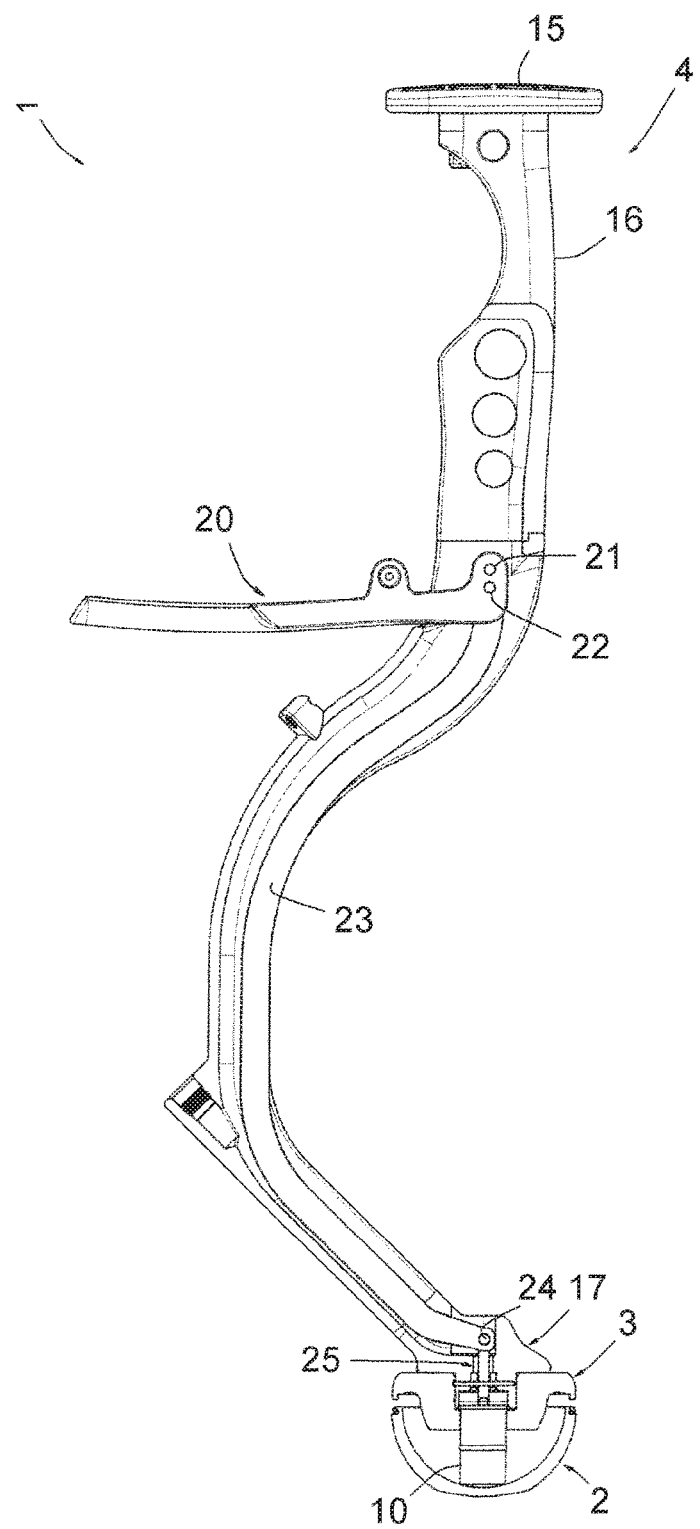
FIG. 2 is a view similar to FIG. 1, in a second position of the lever.
Figure 9:
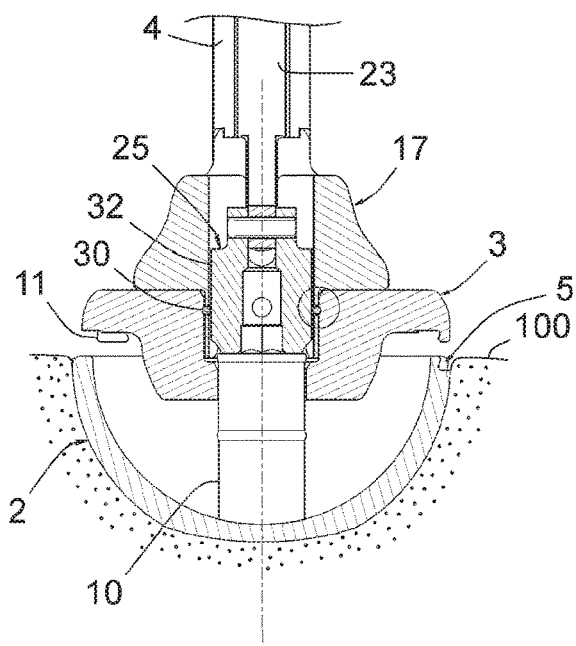
FIGS. 9 and 9A are views similar to FIGS. 8 and 8A, respectively, in a locked assembly position of said assembly head to the gripper and in a position of ejection of the acetabular cup.
Figure 10:
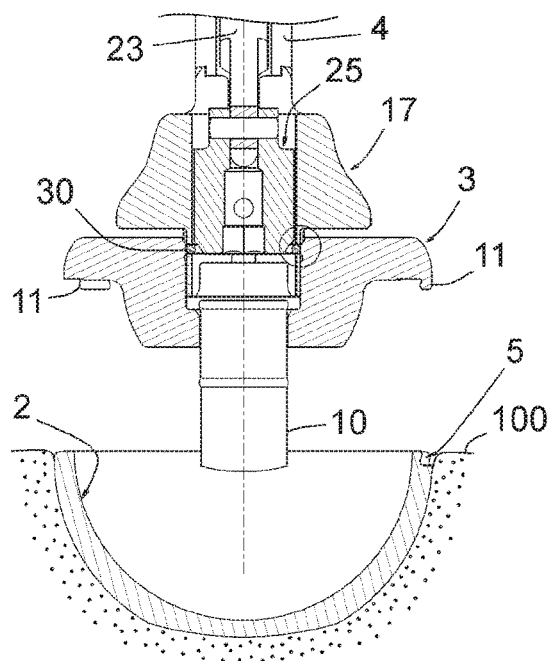
FIGS. 10 and 10A are views similar to FIGS. 9 and 9A, respectively, in a return position of said assembly head and said gripper to an unlocked assembly position, while the acetabular cup has been ejected.
Figure 10A:
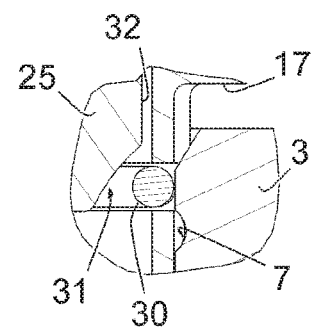

FIGS. 1 and 2 show an assembly 1 for implanting a prosthetic acetabular cup 2 in a cotyloid cavity, this cavity being defined by the pelvis bone 100 of a patient, as shown diagrammatically in FIGS. 9 and 10.

In addition to the acetabular cup 2, the assembly 1 comprises a gripper 3 and a handle 4.

The acetabular cup 2 is formed, in a manner well known in itself, by a metal shell having, in the illustrated example, a substantially hemispherical shape and a smooth and continuous wall. The cavity inwardly defined by this acetabular cup 2 is intended to receive a sliding core (not shown), in particular made from high-density polyethylene, forming an articulation cavity for a femoral head supported by a femoral rod implanted in the femur.

The acetabular cup 2 has, at its equatorial edge and at its outer face, five recesses 5 regularly distributed over its circumference, forming rounded snapping ribs, visible in FIGS. 9 and 10.

Figure 4:
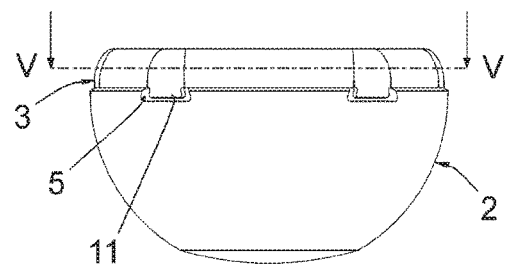
FIG. 4 is an enlarged side view of a gripper and acetabular cup that it comprises.

The gripper 3, more particularly visible in FIG. 4 and following, is formed by a single piece of molded or machined synthetic material. It comprises a flat proximal part 3a and a distal axial boss 3b, and forms an assembly cavity 6. At the walls defining the cavity 6, first elongated recesses 7 are arranged.

The flat proximal part 3a forms a peripheral surface intended to bear against the equatorial rim of the acetabular cavity 2, and the distal axial boss 2b forms an axial bore, in which a pusher 10 is slidingly engaged.

Figure 5:
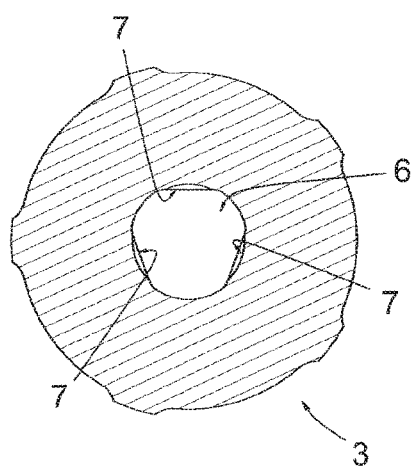
FIG. 5 is a sectional view of the gripper along line V-V of FIG. 4.

It appears that this pusher 10 is formed by a cylindrical part having two circular ribs protruding from its wall, these ribs being situated at a distance from one another. As appears by comparing FIGS. 7 and 9, this distance is slightly larger than a travel of the pusher 10 between a withdrawn position shown in FIG. 5 and an extension position shown in FIG. 7.

It will also be understood that the material making up the pusher 10 and/or the gripper 3 is slightly elastically deformable, so as to allow the forced engagement of the distal circular ribs through said bore, the retention of the pusher 10 on the gripper 3 resulting from the elastic return of the material making up the gripper 3 around the wall portion of the pusher 10 situated between the two ribs. To facilitate the engagement of said rib, the gripper 3 forms an inlet basin at the walls defining the bottom of the cavity 6.

The gripper 3 also comprises, at the peripheral edge of its proximal part 3a, snapping teeth 11 intended to match recesses 5, these teeth 11 forming rounded inner ribs intended to engage by snapping with the ribs formed by the wall of the acetabular cup 2 at the recesses 5, as in particular shown in FIGS. 4 and 7.

It appears that, in said withdrawn position of the pusher 10, shown in FIG. 7, the pusher 10 does not hinder the snapping of the teeth 11 on the ribs formed by the acetabular cup 2, and the distal end of the pusher is withdrawn from the bottom of the acetabular cup 2.

It also appears that the rounded shape of the respective rims of the teeth 11 and the acetabular cup 2 allows the snapping engagement to be reversible in that it is released when the pusher 10 is moved toward its extension position and therefore bears against the bottom of the acetabular cup 2, as will be understood by comparing FIGS. 7 and 9.

In reference again to FIGS. 1 and 2, it appears that the handle 4 comprises a proximal anvil 15, a gripping handle 16 and an assembly head 17 for assembly to the gripper 3.

The anvil 15 is intended to be struck using a mallet during the impacting of the acetabular cup 2 in the cotyloid cavity, while the handle 4 is maintained using the grip 16.

As shown, the handle 4 is equipped, at this grip 16, with a lever 20 mounted pivoting around a pin 21, which lever 20 is pivotably connected, using a pin 22 separate from the pin 21 and having an axis different from the latter, to a connecting rod 23. On the side of the head 17, the connecting rod 23 is connected to a locking/thrust part 25, movable inside the head 17, using a pin 24.

Due to the shift of the two pins 21 and 22, it will be understood that the pivoting of the lever 20 from the position shown in FIG. 1 toward the position shown in FIG. 2 causes a translation of the connecting rod 23 in the distal direction, which is transmitted to the locking/thrust part 25 and moves that part through the head 17, as described later.

Figure 3:
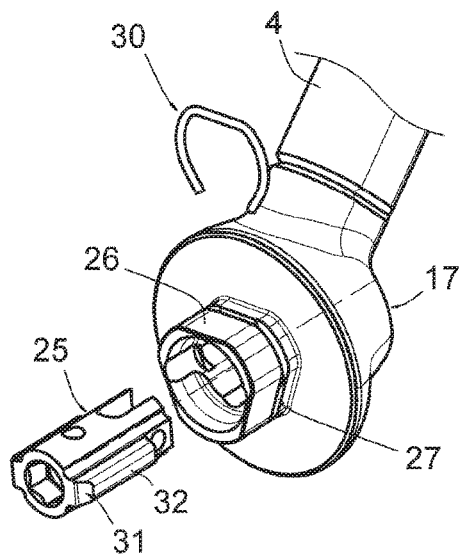
FIG. 3 is an enlarged perspective view of an assembly head that it comprises.

In reference to FIGS. 3, 7 and 8, it appears that the head 17 has an axial extension 26 being integral therewith, capable to be engaged in the cavity 6 in an adjusted manner. This axial extension 26 has recesses 27, in which an elastically deformable metal shank 30 is placed.

As shown in FIG. 3, this shank is U-shaped, having an intermediate rectilinear branch and two curved side branches, and is engaged in the recesses 27. It appears in FIG. 6 that the side branches of the shank 30 are configured so as to be capable to engage in the recesses 7 formed by the gripper 3 at its walls defining said cavity. This shank 30 is deformable between a normal, non-deformed state, visible in FIGS. 3 and 6, and a contracted state, in which its side branches are closer to one another, inside the recesses 27, the latter having a depth of allowing this closer position of said side branches, as shown in FIGS. 7A and 8A.

It further appears that the extension 26 forms, on its distal side, a surrounding end-piece capable to engage on the proximal end of the pusher 10.

Figure 6:
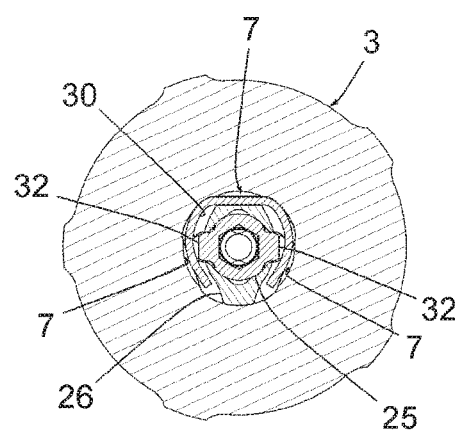
FIG. 6 is a view of the gripper similar to FIG. 5, after engagement of an extension comprised by the assembly head in a cavity comprised by the gripper.

As shown in FIGS. 3, 6 and 7A, the locking/thrust part 25 has two side rims situated on two opposite sides, which are beveled at their distal ends so as to form recesses 31 and which have, on the proximal side relative to these recesses 31 and immediately above them, outer faces forming flats 32.

As shown in FIGS. 7 and 7A, before the handle 4 is assembled to the gripper 3, the shank 30 is in its non-deformed state, in which it partially protrudes beyond the wall of the extension 26 (see FIG. 7A); when the extension 26 is engaged in the cavity 6, the side branches of the shank 30 encounter the walls of the gripper 3 defining the cavity 6 and are therefore brought closer to one another while being moved in the bottom of the recesses 27. When the head 17 is in the position assembled to the gripper 3, as shown in FIGS. 8 and 8A, the recesses 27 come opposite the recesses 7 and the shank 30 then tends to regain its original shape by elastic return, such that its side branches engage both in the recesses 27 and in the recesses 7 (see FIG. 8A).

The handle 4 is then connected to the gripper 3, this connection being sufficient to grasp the gripper 3-acetabular cup 2 assembly and bring this assembly toward the cotyloid cavity to be equipped. This connection is, however, reversible because of the rounded shapes that the recesses 7 and the shank 30 have in cross-section, such that the separation of the gripper 3-acetabular cup 2 assembly with respect to the handle 4 remains possible if necessary.

Figure 9A:
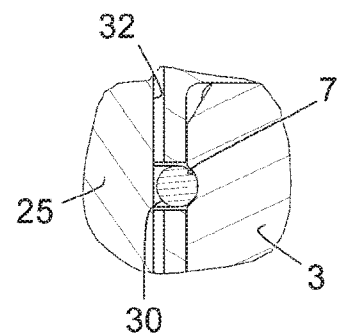

Once the acetabular cup 2 is impacted in the cotyloid cavity, the practitioner acts on the lever 2 so as to move the locking/thrust part 25 in the distal direction, which, over a first part of the travel of this part 25, brings the flats 32 across from the side branches of the shank 30 and keeps these side branches engaged in the recesses 7, as shown in FIG. 9A; the connection between the handle 4 and the gripper 3 is thus locked. Over the second part of the travel of the part 25 in the distal direction, and while the flats 32 are still across from the side branches of the shank 30, the part 25 bears against the proximal end of the pusher 10 and moves the latter. During this movement, the distal end of the pusher 10 encounters the bottom of the acetabular cup 2 and bears against this bottom so as to release the acetabular cup 2 with respect to the teeth 11.

Consequently, the connection of the gripper 3 to the handle 4 is locked before the force necessary to eject the acetabular cup 2 begins to be exerted on the connection of the acetabular cup 2 to the gripper 3.

As appears from the preceding, the invention provides an assembly for implanting an acetabular cup in a cotyloid cavity having decisive advantages with respect to its counterpart assemblies of the prior art. Indeed, because the gripper 3 is formed by a subassembly that can be separated from the handle 4, it has a simpler structure, making it possible for this gripper to be intended for a single use, which greatly reduces the sterilization requirements, which then only pertain to the handle. Furthermore, the assembly according to the invention allows the acetabular cup to be ejected with respect to the gripper, therefore allowing a separation of the instrument and the acetabular cup that does not risk affecting the position of the acetabular cup in the equipped cavity.

What is claimed is:

1. An assembly for implanting an acetabular cup in a cotyloid cavity, the assembly comprising:
    the acetabular cup, intended to be implanted in a cotyloid cavity of a patient's pelvis, and
    a gripping and impacting instrument for the acetabular cup, the instrument comprising:
    a gripper having a surface to come into contact with the acetabular cup, the gripper includes reversible retaining members for reversibly retaining the acetabular cup, and a gripping/impacting handle;
    the acetabular cup has at least two snapping rims;
    the gripper is separated from the handle and capable to be assembled to said handle, the gripper comprising a connecting device to the handle;
    the handle is a separate subassembly from the gripper and capable to be assembled to the gripper, the handle comprising a connecting piece for connecting to the gripper, capable to cooperate with the connecting device of the gripper to connect said handle to said gripper;
    the reversible retaining members are in the form of snapping teeth suitable for engaging with the snapping rims comprised by the acetabular cup and releasing the acetabular cup following a thrust exerted on the acetabular cup along an axis of revolution of that acetabular cup;
    the gripper comprises a movable pusher, movable from a withdrawn position not hindering the assembly of the acetabular cup to the gripper, toward an extension position, the pusher exerting, during the movement, thrust on the acetabular cup along the axis of revolution of said acetabular cup, so as to disengage the snapping rims comprised by the acetabular cup from the engagement with the snapping teeth comprised by the gripper;
    the assembly comprises actuating devices for actuating the movable pusher, making it possible to move that pusher from said withdrawn position to said extension position;
wherein:
    the connecting device for connecting the gripper to the handle comprises:
    an assembly cavity arranged in the gripper and an assembly head secured to the handle, the assembly head forming an extension capable to be received in an adjusted manner in the assembly cavity;
    first locking recesses arranged in walls defining said assembly cavity and second locking recesses arranged in side walls of said extension, the first and second recesses coming opposite one another in the assembly position of the gripper to the handle;
    a movable locking/thrust part, capable to be moved in said extension, that forms third recesses capable to come opposite said second recesses, and that has flats situated near the third recesses, on the proximal side relative thereto;
    an elastically deformable shank or other similar expansive element, engaged and retained in said first recesses or in said second recesses, the shank being deformable between a contracted state, in which does not hinder the engagement and sliding of said extension in said assembly cavity, and a not deformed state, in which extends both in said first recesses and in said second recesses, thus performing a reversible retention of said extension in said assembly cavity and therefore a reversible assembly of the gripper to the handle;
    wherein said locking/thrust part being movable between a position not locking the assembly of the gripper to the handle, in which said third recesses are opposite the shank and allow the deformation of said shank in said contracted state, therefore allowing said reversible assembly of the gripper to the handle, and a position locking the assembly of the gripper to the handle, in which said flats comprised by a locking/thrust part are opposite the shank and prohibit the deformation of said shank in said contracted state, therefore locking the assembly of the gripper to the handle;
    said movable pusher is situated opposite said assembly cavity; and
    the actuating device of the pusher include said locking/thrust part, which is movable between said locking position and a bearing position in which bears against the movable pusher so as to move said pusher toward said extension position.

* * * * *